(12) United States Patent
Moore et al.

(10) Patent No.: US 7,547,732 B2
(45) Date of Patent: Jun. 16, 2009

(54) COMPOSITIONS OF FLUOROCHEMICAL SURFACTANTS

(75) Inventors: George G. I. Moore, Afton, MN (US); William M. Lamanna, Stillwater, MN (US); Michael S. Terrazas, Prescott, WI (US); Rudolf J. Dams, Antwerp (BE); Johan E. De Witte, Westmalle (BE)

(73) Assignee: 3M Innovative Properties Company, St. Paul, MN (US)

( * ) Notice: Subject to any disclaimer, the term of this patent is extended or adjusted under 35 U.S.C. 154(b) by 603 days.

(21) Appl. No.: 11/215,077

(22) Filed: Aug. 30, 2005

(65) Prior Publication Data

US 2007/0049646 A1    Mar. 1, 2007

(51) Int. Cl.
*C07C 143/70* (2006.01)

(52) U.S. Cl. .................. 516/201; 516/203; 516/198

(58) Field of Classification Search .............. 516/201
See application file for complete search history.

(56) References Cited

U.S. PATENT DOCUMENTS

| | | | | |
|---|---|---|---|---|
| 2,809,990 | A | * | 10/1957 | Brown .................. 562/556 |
| 3,829,466 | A | * | 8/1974 | Staffe et al. .................. 560/196 |
| 3,864,396 | A | * | 2/1975 | Staffe et al. .................... 564/48 |
| 3,906,027 | A | * | 9/1975 | Meussdoerffer et al. ...... 560/12 |
| 3,971,373 | A | | 7/1976 | Braun |
| 4,100,324 | A | | 7/1978 | Anderson et al. |
| 4,167,639 | A | | 9/1979 | Billenstein et al. |
| 4,175,096 | A | * | 11/1979 | Reitz et al. ..................... 564/96 |
| 4,252,878 | A | | 2/1981 | Lazarz et al. |
| 4,429,001 | A | | 1/1984 | Kolpin et al. |
| 4,619,976 | A | | 10/1986 | Morris et al. |
| 4,843,134 | A | | 6/1989 | Kotnour et al. |
| 5,342,986 | A | | 8/1994 | Pohmer et al. |
| 5,502,251 | A | | 3/1996 | Pohmer et al. |
| 5,688,884 | A | | 11/1997 | Baker et al. |
| 5,882,762 | A | | 3/1999 | Goeman |
| 6,048,952 | A | | 4/2000 | Behr et al. |
| 6,365,769 | B1 | | 4/2002 | Behr et al. |
| 6,426,025 | B1 | | 7/2002 | Goeman |
| 6,476,114 | B2 | | 11/2002 | Goeman et al. |
| 6,664,354 | B2 | * | 12/2003 | Savu et al. .................. 526/243 |

FOREIGN PATENT DOCUMENTS

| | | |
|---|---|---|
| JP | 2003-294941 | 10/2003 |
| JP | 2004-130306 | 4/2004 |
| JP | 2004-143145 | 5/2004 |
| JP | 2004-143245 | 5/2004 |

OTHER PUBLICATIONS

Kausch, C. M. et al., "Surface Tension and Adsorption Properties of a Series of Bolaamphiphilic Poly(fluorooxetane)s", Langmuir, (2003), pp. 7182-7187, vol. 19, American Chemical Society.

Wente, V. A., "Superfine Thermoplastic Fibers", Industrial and Engineering Chemistry, (Aug. 1956), pp. 1342-1346, vol. 48, Naval Research Laboratory, Washington 25, D.C.

Wente, V. A. et al., "Manufacture of Superfine Organic Fibers", Naval Research Laboratory Report No. 4364, (May 25, 1954), pp. 1-15, Naval Research Laboratory, Washington, D.C.

Karsa, D. R., *Industrial Applications of Surfactants IV,* (1999), The Royal Society of Chemistry, Cambridge CB4 4WF, UK.

Rosen, M. J., *Surfactants and Interfacial Phenomena,* (1989), $2^{nd}$ Edition, John Wiley & Sons, Inc., New York.

Kissa, E., *Fluorinated Surfactants, Synthesis, Properties, Applications,* (1994), Surfactant Science Series, vol. 50, Marcel Dekker, Inc., New York.

Menger, F. M., et al., "Gemini Surfactants", Angew. Chem. Int. Ed., (2000), pp. 1906-1920, vol. 39, Wiley-VCH Verlag GmbH, D-69451 Weinheim.

Oda, R. et al., "Aggregation Properties and Mixing Behavior of Hydrocarbon, Fluorocarbon, and Hybrid Hydrocarbon-Fluorocarbon Cationic Dimeric Surfactants", Langmuir, (2000), pp. 9759-9769, vol. 16, American Chemical Society.

U.S. Appl. No. 11/027,404, Dams et al., entitled "Compositions Containing C4-Swallow Tail Silanes", filed Dec. 30, 2004.

* cited by examiner

*Primary Examiner*—Ling-Siu Choi
*Assistant Examiner*—Chun-Cheng Wang
(74) *Attorney, Agent, or Firm*—Kent S. Kokko

(57) ABSTRACT

Described are monomeric fluorochemical surfactants having two perfluoroalkyl sulfonamido segments and two hydrophilic group, which are more efficient and effective in lowering the surface tension of organic solvents and water compared to other $C_4$-based fluorochemical surfactants.

23 Claims, No Drawings

COMPOSITIONS OF FLUOROCHEMICAL SURFACTANTS

FIELD OF THE INVENTION

The invention relates to novel fluorochemical surfactants comprising two perfluoroalkyl groups and two hydrophilic groups. The fluorochemical surfactants have been found to be more efficient and effective in lowering the surface tension of formulations containing organic solvents and/or water, compared to environmentally sustainable single tail $C_4$-based fluorochemical surfactants.

BACKGROUND OF THE INVENTION

Fluorosurfactants are known and described generally in "Fluorinated Surfactants" by E. Kissa, Surfactants Science Series, Vol. 50 (Marcel Dekker, New York 1994). Fluorosurfactants including those derived from $C_4$ perfluoroalkyl groups are also described in U.S. Pat. Nos. 4,167,639, 3,906,027, 5,342,986 and 5,502,251. In particular, fluorochemical surfactants derived from nonafluorobutanesulfonyl fluoride (PBSF) have been described more recently in U.S. Pat. No. 6,664,354 (Savu et al.) stating that the PBSF-derived surfactants are almost as effective as the known premier surfactants derived from perfluorooctanesulfonyl fluoride (POSF). Furthermore, such surfactants have been described as more environmentally friendly. There remains a need to improve on the effectiveness and efficiency of such PBSF-derived fluorochemical surfactants, while maintaining environmental sustainability.

SUMMARY OF THE INVENTION

It has been discovered that fluorochemical surfactants having two perfluoroalkyl groups in proximity to one another, preferably $C_3$-$C_6$ perfluoroalkyl groups, are more effective and efficient in lowering the surface tension of formulations containing organic solvents and water, compared to other fluorochemical surfactants containing a single perfluoroalkyl group. The surfactants of the invention can be used as additives in paints, lacquers, inks, coatings, fire fighting agents and the like, including water- and solvent based formulations. They may also provide superior leveling and wetting to floor finish coatings. They can be more economical to make.

The surfactants of the invention may be substantially free (i.e. less than 1 wt. %) of fluorochemical compounds that eliminate slowly from living organisms and are therefore considered environmentally sustainable versus most other known commercially available fluorochemical materials, which are based on surfactants containing longer perfluorinated segments or tails.

Many previously known fluorochemical materials contain perfluorooctyl moieties. These surfactants ultimately degrade to perfluorooctyl-containing compounds. It has been reported that certain perfluorooctyl-containing compounds may tend to bio-accumulate in living organisms; this tendency has been cited as a potential concern regarding some fluorochemical compounds. For example, see U.S. Pat. No. 5,688,884 (Baker et al.). As a result, there is a desire for fluorochemical surfactant-containing compositions which are effective in providing desired surfactant properties, and which eliminate more effectively from the body (including the composition and its degradation products).

It is expected that the fluorochemical surfactants of the present invention, which contain $C_3$-$C_6$ perfluoroalkyl moieties, when exposed to biologic, thermal, oxidative, hydrolytic, and photolytic conditions found in the environment, will break down to various degradation products. For example, compositions comprising perfluorobutylsulfonamido moieties are expected to degrade, at least to some extent, ultimately to perfluorobutylsulfonate salts. It has been surprisingly found that perfluorobutylsulfonate, tested in the form of its potassium salt, eliminates from the body more effectively than perfluorohexylsulfonate and much more effectively than perfluorooctylsulfonate.

Accordingly, one aspect of the present invention provides a fluorochemical surfactant comprising one or more compounds of Formula I:

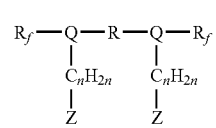

wherein each $R_f$ is a fluoroalkyl group, preferably a $C_3$-$C_6$ perfluoroalkyl group, and most preferably is a $C_4$ perfluoroalkyl group, i.e. $C_4F_9$—.

R is a divalent organic linking group,

Q is a trivalent group selected from —$SO_2N(-)(-)$, —$(CH_2)_pCH(O—)(-)$, —$(CH_2)_p$—$CH(-)(-)$, and —$(CH_2)_p$—$CH(O—)(CH_2)_pO$—, where each p is an integer of 1 to 11, preferably 1 to 6;

Z is a hydrophilic group, and each n is 0 to 11, preferably 0 to 6.

Another aspect of the invention is a surfactant composition including one or more fluorochemical surfactants of Formula I in a solvent, which can be aqueous or organic and further optionally an auxiliary surfactant, including hydrocarbon or silicone based surfactants, known to those skilled in the art.

A further aspect of the invention is a method of reducing the surface tension of a liquid by adding to said liquid a surfactant composition as above defined. Still another aspect of the invention is a method of improving the wetting of a coating mixture on a substrate by adding to the coating mixture a surfactant composition as defined above.

As used herein:

"alkyl" and "alkylene" mean the monovalent and divalent residues remaining after removal of one and two hydrogen atoms, respectively, from a linear or branched chain saturated hydrocarbon (alkane) having 1 to 20 carbon atoms;

"alkenylene" means the divalent residues remaining after removal of two hydrogen atoms from a linear or branched chain unsaturated hydrocarbon (alkene) having 2 to 20 carbon atoms, i.e. —CH=CH—, and the like.

"alkynylene" means the divalent residues remaining after removal of two vinylic hydrogen atoms from a linear or branched chain unsaturated hydrocarbon (alkyne) having 2 to 20 carbon atoms; e.g. —C≡C—, —$CH_2$—C≡C— and the like.

"lower alkyl" means $C_1$ to $C_4$ alkyl;

"aryl" and "arylene" mean the monovalent and divalent residues remaining after removal of one and two hydrogen atoms, respectively, from an aromatic compound (single ring and multi- and fused-rings) having 5 to 12 ring atoms and includes substituted aromatics such as lower alkaryl and aralkyl, lower alkoxy, N,N-di(lower alkyl)amino, nitro, cyano, halo, and lower alkyl carboxylic ester, wherein "lower" means $C_1$ to $C_4$.

"cycloalkyl" and "cycloalkylene" mean the monovalent and divalent residues remaining after removal of one and two hydrogen atoms, respectively, from a cyclic hydrocarbon having 3 to 12 carbon atoms;

"perfluoroalkyl" means an alkyl having all or essentially all of the hydrogen atoms of the alkyl group replaced by fluorine atoms and the number of carbon atoms is from 1 to about 12, e.g. perfluoropropyl, perfluorobutyl, perfluorooctyl, and the like.

DETAILED DESCRIPTION

The present invention provides fluorochemical surfactants comprising one or more compounds of Formula I:

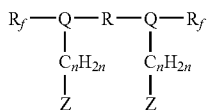
I wherein
each $R_f$ is a fluoroalkyl group, preferably a $C_3$-$C_6$ perfluoroalkyl group, and most preferably is a $C_4$ perfluoroalkyl group, i.e. $C_4F_9$—.
R is a divalent organic linking group,
Q is a trivalent group selected from —$SO_2N(-)(-)$, —$(CH_2)_pCH(O-)(-)$, —$(CH_2)_p$—CH(-)(-), and —$(CH_2)_p$—CH(O—)($CH_2)_pO$—, where each p is an integer of 1 to 11, preferably 1 to 6;
Z is a hydrophilic group, and
each n is 0 to 11, preferably 0 to 6.

In one particular embodiment, the present invention provides fluorochemical surfactants of the formula:

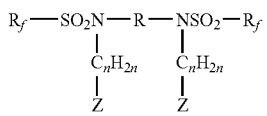
II wherein
each $R_f$ is a fluoroalkyl group,
R is a divalent organic linking group,
Z is a hydrophilic group, and
each n is 0 to 11, preferably 0 to 6.

In another embodiment, the present invention provides fluorochemical surfactants of the formula:

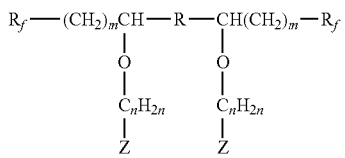
III wherein
each $R_f$ is a fluoroalkyl group,
R is a divalent organic linking group,
Z is a hydrophilic group,
each m is 1 to 11, preferably 1 to 6; and
each n is 0 to 11, preferably 0 to 6.

With respect to Formulas I to III, $R_f$ may be any $C_3$-$C_{12}$ linear or branched perfluoroalkyl group. Preferably, due to environmental and biological concerns, $R_f$ is selected from $C_3$-$C_6$ perfluoroalkyl groups, and most preferably, $R_f$ is selected from $C_4$, perfluoroalkyl groups, i.e. perfluorobutyl groups.

R is a divalent organic linking group, preferably selected from a divalent aliphatic, cycloaliphatic, or aromatic group, and combinations thereof, such as aralkylene, or alkarylene. When R is an aliphatic group, alkylene, alkenylene, or alkynylene are contemplated, and may be further substitute with one or more catenary oxygen or nitrogen atoms, i.e. —O— or —NR'—. Where R' is an H or lower alkyl;

Z may be any hydrophilic group that provides the desired degree of solubility to the compounds of Formula I to III in water, an organic solvent (or combination thereof). Preferably, Z is selected from carboxyl, poly(oxyalkylene), sulfonate, sulfate, phosphate, and quaternary ammonium groups.

In one embodiment, the poly(oxyalkylene) group (Z) is a poly(oxyethylene) oligomer or (co)polymer, i.e. containing units of the formula —(O—$C_2H_4$)—. As used herein, oligomer refers to polymers having two to twenty repeat units. In another embodiment, the pendent poly(alkylene oxide) group is a poly(ethylene oxide-co-propylene oxide) copolymer, i.e. containing units of the formulas —(O—$C_2H_4$)— and —(O—$C_3H_6$)—. Such copolymers may be block copolymers, random copolymers, or gradient copolymers.

In one particular embodiment of the surfactant, the hydrophilic group is of the formula A or B, where EO is an ethyleneoxy and PO is a propyleneoxy group:

$$—(EO)_s—(PO)_t—(EO)_s—R' \quad \text{or} \quad (A)$$

$$—(PO)_t—(EO)_s—(PO)_t—R' \quad (B)$$

wherein R' is H or a lower alkyl group, s is an integer of 1 to about 20 and t is an integer of 0 to about 20.

Alternatively, another embodiment comprises a poly(oxyalkylene) group where the poly(oxyalkylene) group is derived from a polyalkylene oxide of formula A where t is an integer of about 9 to about 15 and s is an integer of about 9 to about 20.

Z may comprise a water-solubilizing polar group that may be anionic, nonionic, cationic or amphoteric. Preferred anionic groups include, but are not limited to, sulfonates (e.g., —$SO_3M$), sulfates (e.g., —$OSO_3M$), and carboxylates (e.g., —C(=O)OM), wherein M is hydrogen, a metal cation such as an alkali or alkaline earth metal cation (e.g., sodium, potassium, calcium or magnesium, and the like), or a nitrogen-based cation, such as, for example, ammonium, including quaternary ammonium cations and protonated amines of the formula —$N^+(R^1)_3Y^-$, where $Y^-$ is an anion, $R^1$ is a hydrogen or a $C_1$-$C_4$ alkyl group. Y may be a halide, e.g., fluoro, chloro, bromo, or iodo or a carboxylate, e.g., an anion of a carboxylic acid of 1-8 carbon atoms. Preferred Y groups are chloro, iodo or acetate.

Particularly useful compounds of Formula I to III are $C_4F_9SO_2N(C_nH_{2n}COOM)C_mH_{2m}N(C_nH_{2n}COOM)SO_2C_4F_9$ where m is 2 to 6 and n is 1 to 4, such as $C_4F_9SO_2N(CH_2COOM)$—$CH_2CH_2CH_2CH_2CH_2CH_2N(CH_2COOM)SO_2C_4F_9$, where M is an organic or inorganic cation, and $C_4F_9CH_2CH(O(CH_2CH_2O)_nH)CH_2OCH_2C$≡$CCCH_2OCH_2CH(O—(CH_2CH_2O)_mH)CH_2C_4F_9$ wherein n and m represent numbers from 0 to 50, with the proviso that n+m is at least 2.

Compounds of Formula II may be prepared by sulfonylation of a diamine with two equivalents of a perfluoroalkylsulfonyl halide, followed by alkylation with (for example) an haloalkyl carboxylate (such as an Ω-haloalkyl carboxylate) as shown in the following general Scheme I. Alternatively, a diamine may be first alkylated with the haloalkyl carboxylate followed by a perfluoroalkylsulfonyl halide.

Scheme III. Perfluoroalkyl iodides may be made by the procedures described in U.S. Pat. No. 6,048,952 and U.S. Pat. No. 6,365,769 (Behr et al.) incorporated herein by reference. The di-iodides may also be reacted with amines to form quaternary ammonium salt surfactants.

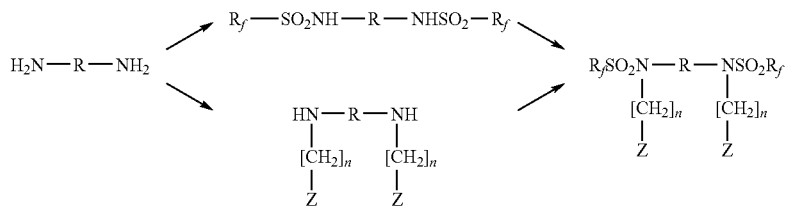

Scheme I

In another alternative, two equivalents of a sulfonamido anion may be reacted with a dihalide as shown in Scheme II:

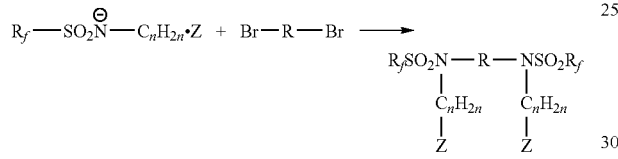

Scheme II

Compounds of Formula III, may be prepared by reaction of a perfluoroalkyl epoxy compound with a diol (HO—R—OH) to produce a bis-fluoroalkyl diol. This product may then be reacted with (for example) ethylene oxide to produce a bis-poly(alkyleneoxy) compound, with an haloalkyl carboxylate to produce a bis-carboxylate, with sultone, such as propane sultone, to produce a sulfonate, with chlorosulfonic acid to produce a sulfate, with a chloroalkyl sulfonic acid to produce a sulfonate, or with phosphorus oxychloride to produce a phosphate as shown in Scheme III. The fluoroalkyl epoxy compounds may be prepared as described in U.S. Pat. No. 6,048,952 and U.S. Pat. No. 6,365,769 (Behr et al.) incorporated herein by reference. Scheme III can also be practiced with readily available N-glycidyl sulfonamides.

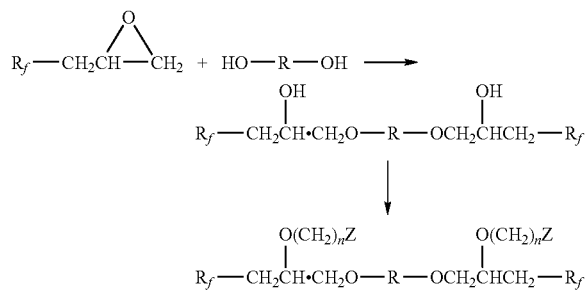

Scheme III

Alternatively, a fluoroalkyl iodide compound may be reacted with a diolefin to produce an intermediate di-iodide. This may be converted to a diol, then reacted as previously describe to incorporate the indicated Z groups as shown in

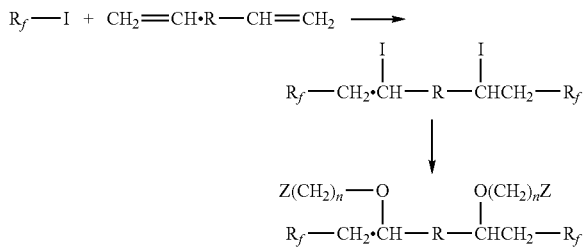

Scheme IV

The surfactants of the present invention have similar beneficial properties and can be used for the same purposes as surfactants with a single perfluoroalkyl group and the premier surfactants, such as corresponding perfluorooctanesulfonamido surfactants. Surprisingly, the surfactants of the present invention are more efficient and effective in lowering the surface tension of formulations containing organic solvents and water than other environmentally sustainable $C_4$-based fluorochemical surfactants, having a single perfluoroalkyl group.

Similarly, the surfactants of the present invention can improve the wetting and leveling of a liquid or coating mixture on a substrate to an extent comparable to the other $C_8$-fluorochemical surfactants and generally do so with less foaming. The surfactants of this invention can be used individually or in combination with hydrocarbon or silicone surfactants to produce the desired surface tension reduction or wetting improvement. Useful auxiliary surfactants may be found with reference to Industrial Applications Of Surfactants, D. R. Karsa, Ed., Royal Society of Chemistry, London, and M. Rosen, Surfactants and Interfacial Phenomena, Wiley-Interscience, New York.

Fluorochemical surfactants of the present invention have been found to be surprisingly effective in a number of applications. For example the fluorochemical surfactants of the present invention may be used as coating additives to provide better wetting and leveling of the coating to a substrate surface, or better wetting and leveling of a component within the coating formulation, for example, enhancing the wetting characteristics of a thickening agent.

When used in water borne coatings, the fluorochemical surfactants are formulated into an aqueous solution or dispersion at a final concentration of about 0.001 to about 0.5, preferably 0.01 to 0.3, weight percent based on the weight of the solution or dispersion. The formulated product can be used in many coating applications such as floor polishes and finishes, varnish for a variety substrates, including wood floors, water borne gel applied in the manufacture of photographic film, automotive topcoats, and marine coatings.

The fluorochemical surfactants can be used in other protective thin layer coatings as well, by preparing a formulation containing a surfactant, a powder, or a liquid mixture with organic solvents, fillers, and an organic resin including but not limited to epoxies, urethanes, polycarbonate-urethanes, acrylics, and the like. Typically, the surfactant concentration is about 0.001 to 0.5 wt. %, preferably 0.01 to about 0.3 wt. %, based on the weight of the formulation. Specific uses for these protective coatings include, for example, corrosion resistance coatings on electronic components for the computer and telecommunications industry, signage, office brushing, spraying, flow coating, and the like. The coatings are typically applied, dried, and cured, leaving the finished product with a solid coating. As an example, the surfactants have been found to be extremely effective in providing smooth clear polymer coatings without coating defects on surfaces that are difficult to wet, such as oily surfaces.

The fluorochemical surfactants of the invention are particularly suitable for use with aqueous (waterborne) polyurethanes and acrylics to improve the film-forming properties and the quality of the resulting finish. Aqueous polyurethanes and acrylics are binary colloidal systems in which a discontinuous polymer phase is dispersed in a continuous aqueous phase. Aqueous polyurethane and acrylic dispersions are known, and are becoming increasingly important in coating and adhesive applications due to environmental and safety regulations of organic solvent based systems. The dispersions can be formulated using little or no co-solvent to produce high performance coatings and adhesives at ambient temperatures. They not only replace organic solutions but find applications in new areas as well. For instance, they are not aggressive towards plastic surfaces and provide excellent adhesion to glass and polymeric fibers due to their ionomeric nature. However, their use in some applications has been limited by the lower quality of the resulting finish relative to conventional solvent-borne and acrylics.

Aqueous polymer dispersions are generally prepared by incorporating the fluorochemical surfactants of the invention into the polymer coating composition. A very stable dispersion results. Stability of the dispersion is the result of the electrostatic repulsion of like charges associated with different particles, and steric stabilization. Particle size in stable film forming dispersions is generally 30-800 nm. The viscosity of the dispersion is dependent on the polymer particle size and solids content, degree of phase separation and independent of the polymer molecular weight (MW).

During film formation of polymer dispersions, water evaporates and the poly polymer particles coalesce to form a continuous film. The addition of the fluorochemical surfactants of the invention, optionally with high boiling cosolvents such as dipropyleneglycol monomethylether, improves the film forming properties in some systems. Film formation properties also improve with elevated temperatures. The physical properties of the film are controlled by the selection of starting materials.

In still other applications, the fluorochemical surfactants of the present invention may be used as wetting and leveling agents or additives in photoresists, developers, and cleaning solutions in the manufacture of electronic materials. When used in photoresists, the surfactants provide a dramatic decrease in defect densities. The surfactant is mixed in a solvent solution to a final concentration of about 0.001 to about 0.5 weight percent based on the weight of the solution, and the mixture is coated onto electronic parts, typically by spin coating. For example, the mixture is dropped onto a wafer while it is spinning, forming an even coating on the wafer. In subsequent processing, a portion of the coating on the wafer is stripped with alkaline cleaners, etched with strongly oxidizing liquids of gases, or removed with solvents such as acetone. The remaining coating is cured on the article.

When used in developer and cleaning solutions, the fluorochemical surfactant enables removal of contaminants from microchannels, which affects resolution and is critical to device operation. The surfactants provide low surface energy and chemical/thermal stability, allowing smaller critical dimensions (increased resolution) in the product as well as improved processor speeds and manufacturability. The fluorochemical surfactant is mixed in an aqueous solution to a final concentration of about 0.001 to about 0.5 weight percent based on the weight of the developer or cleaning solution. The mixture is transferred to a bath, and the electronic parts are either dipped or run through the bath on a conveyor belt.

In a further application, the fluorochemical surfactants of the present invention may be useful in hard surface cleaning solutions to provide improved wetting of the hard surface and the contaminants to be removed. A cleaning solution is formulated to include about 0.001 to about 0.5 weight percent surfactant based on the weight of the cleaning solution. The cleaning solution is placed in a dispensing container such as a spray bottle or refill container for the spray bottle. Upon use, the cleaning solution is sprayed or otherwise applied to a hard surface such as window glass, a mirror, or ceramic tile, and the surface is wiped clean with a paper or fabric wipe. Alternatively, the contaminated part may be immersed or dipped into the cleaning solution.

In yet another application, the fluorochemical surfactants of the present invention may be useful to enhance the wetting characteristics of thickening agents to form gels for solidifying or encapsulating medical waste. The surfactant is mixed with ethanol and applied to partially neutralized polyacrylic acid resin, typically having an average particle size of about 500 to about 800 microns. Other ingredients may be added to eliminate biological hazards and transform biological waste into non-hazardous waste. The ethanol is evaporated and the treated resin (about 0.5 to about 1.5 percent by weight surfactant based on the weight of the resin) in powder form is packaged and ready for use. The resulting product may be used in a variety of ways, including absorption of biological fluids generated, for example, in an operating room, and encapsulation of sharps generated in a host of medical procedures. The powder can be added to biological fluids that wet the resin particles, causing gelation to occur. The sharps can be placed in a container, for example, containing the powder, and when water is added the powder gels around the sharps. In both instances, the container is disposed of as a solid non-hazardous waste.

The fluorochemical surfactants of the present invention may be used as leveling additives for various resist inks for electronics and semiconductors, for inks such as gravure coat, screen print and thermal print, for adhesive layer for wafer polishing and Wafer CMP solutions, for hard coats for plastic lenses, and for lubricant spray coatings. The surfactants may be used as antistatic agents, leveling agents or wetting additives for films such as film condenser, microfilm, medical X-ray film, and APS film. The surfactants of the invention may also be used as wetting and lubricant additives for urethane, epoxy, acrylic, polyimide, and other materials, as foam blowing additives, as finishing additives for dry cleaning, as a leveling additive for pen ink, as thickening/oil barrier additives for grease coatings and grease/PTFE lubricants, as leveling or wetting additives for green house film as stabilizer for fluorochemical emulsions or dispersions.

Some of the fluorochemical surfactants, particularly those containing neutral Z hydrophilic groups, of the invention are also useful as additives to thermoplastic or thermoset polymers to provide desirable hydrophilic properties thereto. Thus the present invention provides a polymer composition comprising a thermoplastic or thermoset polymer the fluorochemical surfactants of the invention dispersed therein. The term "dispersed therein" denotes merely the presence of the fluorochemical surfactants in the thermoplastic polymer without limitation as to where the fluorochemical surfactants is located in the layer. Thus, the fluorochemical surfactants may be uniformly dispersed in the bulk of the polymer or a major portion of the surfactants may have migrated to the surface of the thermoplastic polymer layer. A polymer composition of this invention can be melted or shaped, for example by extrusion or molding, to produce shaped articles, such as fibers, films and molded articles.

The fluorochemical surfactant is typically added in amounts between about 0.001 and about 5% by weight, preferably between about 0.01 and about 0.3% by weight, based on the total weight of polymer.

Useful polymers include both thermoplastic and thermoset polymers and include synthetic linear polyamides, e.g., nylon-6 and nylon-66, polyesters, e.g., polyethylene terephthalate, polyurethanes, epoxides, epoxy resins, acrylates, polystyrenes and polyolefins, e.g., polyethylene and polypropylene. Thermoplastic polymers such as polyolefins are preferred. The resultant articles, due to the presence of the fluorochemical surfactant, have improved hydrophilicity relative to the polymer containing no surfactant.

Shaped articles (e.g., fibers, films and molded or extruded articles) of this invention can be made, e.g., by blending or otherwise uniformly mixing the fluorochemical surfactants and the polymer, for example by intimately mixing the oligomer with pelletized or powdered polymer, and melt extruding the mixture into shaped articles such as pellets, fibers, or films by known methods. The surfactants can be mixed per se with the polymer or can be mixed with the polymer in the form of a "masterbatch" (concentrate) of the surfactants in the polymer. Masterbatches typically contain from about 10% to about 25% by weight of the fluorochemical surfactants. Also, an organic solution of the surfactants may be mixed with the powdered or pelletized polymer, the mixture dried to remove solvent, then melted and extruded into the desired shaped article. Alternatively, molten surfactants (as a compound(s) or masterbatch) can be injected into a molten polymer stream to form a blend just prior to extrusion into the desired shaped article.

When using thermoset resins, such as epoxy resins, urethanes and acrylates, the fluorochemical surfactants may be mixed with the resin and cured by application of heat. Preferably such thermoset resins may be processed by reactive extrusion techniques such as are taught in U.S. Pat. No. 4,619,976 (Kotnour) and U.S. Pat. No. 4,843,134 (Kotnour) the disclosures of which are herein incorporated by reference.

The thermoplastic composition containing fluorochemical surfactants of the present invention may be used to provide hydrophilicity to fibers, films and other shaped articles. The fluorochemical surfactants are generally melt processible, i.e., suffer substantially no degradation under the melt processing conditions used to form the fibers.

The amount of fluorochemical surfactant in the composition is that amount sufficient to produce a shaped article having a surface with the desired properties of oil and water repellency and/or soiling resistance. Preferably, the amount of oligomer will be that amount which provides from about 100 to 10,000 ppm fluorine, more preferably 200 to 5000 ppm, most preferably 400 to 3000 ppm fluorine, based on the weight of the shaped article.

After melt extrusion of a fiber, film or extruded article, an annealing step may be carried out to. Annealing apparently allows the fluorochemical oligomer to migrate to the surface of the thermoplastic polymer with a resultant increase in hydrophilicity, and increased surface activity. The fiber or film is annealed for at a temperature and for a time sufficient to increase the amount of fluorochemical oligomer at the surface. Effective time and temperature will bear an inverse relationship to one another and a wide variety of conditions will be suitable. Using polypropylene, for example, the annealing process can be conducted below the melt temperature at about 50° to 120° C. for a period of about 30 seconds to 10 minutes. Annealing may also be effected by contact with heated rolls, such as embossing rolls, at 50° C. to 160° C. for periods of about 1 to 30 seconds. In some cases, the presence of moisture during annealing, e.g., by using an autoclave to anneal, can improve the effectiveness of the fluorochemical oligomer. The annealing method may also serve to reduce the amount of surfactant necessary by maximizing fluorine content at the surface of the polymer.

As used herein, the terms "fiber" and "fibrous" refer to particulate matter, generally thermoplastic resin, wherein the length to diameter ratio of the particulate matter is greater than or equal to about 10. Fiber diameters may range from about 0.5 micron up to at least 1,000 microns. Each fiber may have a variety of cross-sectional geometries, may be solid or hollow, and may be colored by, e.g., incorporating dye or pigment into the polymer melt prior to extrusion.

The non-woven webs of fibers of thermoplastic olefinic polymer for use in this invention include non-woven webs manufactured by any of the commonly known processes for producing non-woven webs. For example, the fibrous non-woven web can be made by spunbonding techniques or melt-blowing techniques or combinations of the two. Spunbonded fibers are typically small diameter fibers which are formed by extruding molten thermoplastic polymer as filaments from a plurality of fine, usually circular capillaries of a spinneret with the diameter of the extruded fibers being rapidly reduced. Meltblown fibers are typically formed by extruding the molten thermoplastic material through a plurality of fine, usually circular, die capillaries as molten threads or filaments into a high velocity, usually heated gas (e.g. air) stream which attenuates the filaments of molten thermoplastic material to reduce their diameter. Thereafter, the meltblown fibers are carried by the high velocity gas stream and are deposited on a collecting surface to form a web of randomly disbursed meltblown fibers. Any of the non-woven webs may be made from a single type of fiber or two or more fibers that differ in the type of thermoplastic olefinic polymer and/or thickness. Alternatively, sheath-core fibers can be extruded, containing different polymer compositions in each layer or containing the same polymer composition in each layer but employing the more expensive fluorochemical component in the outer layer.

The melt blown polypropylene microfibers useful in the present invention can be prepared as described in Van Wente, A., "Superfine Thermoplastic Fibers," Industrial Engineering Chemistry, vol. 48, pp. 1342-1346 (1956) and in Report No. 4364 of the Naval Research Laboratories, published May 25, 1954, entitled "Manufacture of Super Fine Organic Fibers" by Van Wente et al. or from microfiber webs containing particulate matter such as those disclosed, for example, in U.S.

Pat. No. 3,971,373 (Braun), U.S. Pat. No. 4,100,324 (Anderson) and U.S. Pat. No. 4,429,001 (Kolpin et al.), which patents are incorporated herein by reference.

The above applications are not meant to be limiting but only exemplary. The following section provides working examples that describe in particular and by way of illustration the present invention. These working examples are provided as illustrative and are not to be deemed to be limiting on the invention.

EXAMPLES

Glossary

| Designator | Structure, formula and/or chemical name | Availability |
|---|---|---|
| 1,4 dichloro-2-butyne | $ClCH_2C\equiv CCH_2Cl$ | Sigma-Aldrich |
| $ClCH_2CH_2Cl$ | 1,2-dichloroethane | Sigma-Aldrich |
| DPM | Dipropyleneglycol monomethylether; | Sigma-Aldrich |
| Diisopropylethylamine | $;(CH_3)_2CHNC_2H_5$ | Sigma-Aldrich |
| FC-129 | $C_8F_{17}$ based surfactant | 3M |
| FC-120 | $C_{10}F_{21}$ based surfactant | 3M |
| glycine ethyl ester hydrochloride | $HCl-NH_2CH_2COOC_2H_5$ | Sigma-Aldrich |
| PBCH epoxide |  | May be prepared as described in U.S. Pat. No. 6,365,769 Examples 25 and 26. |
| "MASURF FS-230" | $R_fCH_2CH_2N(CH_3)_2-O$, where $R_f$ includes $C_8F_{17}$ | Mason Chemical |
| $NaOCH_3$ | Sodium methoxide (25% in methanol) | Sigma-Aldrich |
| THF | tetrahydrofuran | Sigma-Aldrich |
| "ZONYL FSH" | $R_fCH_2CH_2O(C_2H_4O)_nH$, where $R_f$ includes $C_8F_{17}$ | DuPont, Wilmington, Delaware |
| "ZONYL FSN" | $R_fCH_2CH_2O(C_2H_4O)_nH$, where $R_f$ includes $C_8F_{17}$ | DuPont |

Preparation of FC-1: $C_4F_9SO_2N(CH_2COOH)C_6H_{12}N(CH_2COOH)SO_2C_4F_9$.

A 500 mL round bottom flask was charged with 1,6-hexamethylenediamine (23.2 g; 0.2 mol; distilled before use), diisopropylethylamine (72.0 g), and THF (150 mL; anhydrous). The mixture was heated to reflux and $C_4F_9SO_2F$ (150.0 g; 0.5 mol) was added over 30 minutes. The resulting white slurry was heated and stirred overnight. The THF was stripped on the rotary evaporator and the white solid was dissolved in dilute NaOH (5%; aqueous), filtered, and acidified with con HCl (concentrated) yielding a white powder (120.0 g) after drying. This was extracted twice with 500 mL boiling toluene and filtration, leaving 38.9 g insoluble salt. On cooling, the toluene yielded a pale yellow solid, dried to 61.7 g, mp 128-31. The latter analyzed as 90% w/w $C_4F_9SO_2NHC_6H_{12}NHSO_2C_4F_9$ by nmr, with 6% $C_4F_9SO_2O^-H_3N^+C_6H_{12}NH_3^{+-}OSO_2C_4F_9$.

A mixture of $C_4F_9SO_2NHC_6H_{12}NHSO_2C_4F_9$ (250 g, 0.368 mol) and 210 granular $Na_2CO_3$ in 1000 L acetone was stirred at reflux for 30 min. and then treated with 130.0 g (0.78 mol) ethyl bromoacetate. Glc at 24 hr showed complete conversion. The mixture was cooled, filtered, the solid washed with acetone, and the acetone solutions stripped to 315.3 g tan oil. This was dissolved in 300 mL warm HOAc and added to 150 ml 18% HCl in a paddle-stirred flask and heated 20 hrs at reflux, final T 99C. The mixture was allowed to cool partially and added with stirring to 1.3 L cold water, forming a light tan solid, collected, washed with water, and dried at 50° C./40 mmHg to 278.8 g. Recrystallization from EtOAc-Tol gave off-white product, 94% pure diacid by nmr, remainder diacid monoethyl ester.

Alternative Route Via Dibromohexane:

A mixture of glycine ethyl ester hydrochloride (56.0 g), diisopropylehylamine (150.0 g), and THF (150 mL)was stirred at near reflux while treated dropwise with $C_4F_9SO_2F$ (131 g). The resulting pale yellow slurry was stirred at reflux for 20 hr, forming a deep maroon solution. This solution was washed with dil HCl twice, water and dried in dichloromethane over $MgSO_4$. On stripping, this yielded 169.4 g brown oil, 70% pure by glc: $C_4F_9SO_2NHCH_2COOEt$. This was dissolved in a solution of 34.9 g 50% NaOH in about 200 mL water. Acidification with dil HCl and extraction gave 139.5 g. Of this, 38.5 g was mixed with 21.6 g 25% NaOMe/MeOH and about 20 mL MeOH. After stripping off volatiles, a solution of 12.2 g 1,6-dibromohexane in 75 mL glyme was added and the mixture was stirred at reflux for 8 hr. Glc indicated incomplete conversion. At 24 hr, low levels of starting material were still present, 0.3 g of 60% NaH/mineral oil was added and reflux was continued for 24 hr. The mixture was washed with water and extracted to a red oil, 27.0 g. Gc/ms showed a major component $C_4F_9SO_2NHCH_2COOMe$, the desired dimethyl ester, the diacid monomethyl ester, and minor materials including the diacid ethyl methyl ester and the bromohexyl derivative of the starting material.

Preparation of FC-2: $C_4F_9SO_2N(CH_2COOH)C_2H4N(CH_2COOH)SO_2C_4F_9$.

A 500 mL round bottom flask fitted with an overhead stirrer was charged with ethylenediamine (15.0 g; freshly distilled from $CaH_2$), diisopropylethylamine (130.0 g), and anhydrous THF (100 mL; anhydrous). While stirring, $C_4F_9SO_2F$ (160.0 g) was added in a slow stream. The slurry was stirred at reflux overnight, stripped on a rotary evaporator, the resulting solid washed with HCl (10%) and filtered to yield 104.4 g $C_4F_9SO_2NHC_2H_4NHSO_2C_4F_9$ (104.4 g). $C_4F_9SO_2NHC_2H_4SO_2C_4F_9$ (12.5 g; 0.02 mol) was stirred at reflux with ethyl bromoacetate (7.2 g; available from Sigma-Aldrich) and 10.0 g $Na_2CO_3$ (10.0 g) in 100 mL acetone for 17 hr. Analysis by glc indicated complete conversion. The slurry was filtered, the acetone stripped using a rotary evaporator, and the resulting solid triturated with hexane to leave a solid. The sold was recrystallized from toluene to 12.8 g. Of this diester, 9.0 g was dissolve din 15 mL ethanol and added to 8.4 g 50% NaOH in 20 mL water, causing formation of a white precipitate. This was left in an open beaker two days, and further acidified with HCl (concentrated). Filtration yielded the solid $C_4F_9SO_2N(CH_2COOH)C_2H_4N(CH_2COOH)SO_2C_4F_9$ (6.6 g).

Preparation of FC-3:

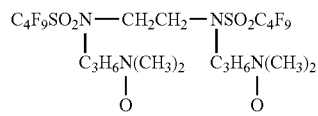

A three-necked 500 mL flask fitted with a stirrer, thermometer, cooler and heating mantle was charged with $C_4F_9SO_2NHCH_2CH_2CH_2N(CH_3)_2$ (63.0 g, 0.16 mol), dry dimethylformamide (50.0 g; dry) and NaOCH$_3$ (35 g; 0.19 mol; 30% in methanol). The mixture was heated at 60° C. reacted for 1 h, and the methanol was distilled from the mixture. ClCH$_2$CH$_2$Cl (7.8 g; 0.08 mol) was added and held at 65° C. overnight. The obtained mixture was filtered and the washed twice with 200 mL water at 80° C. An amber solid product was formed at room temperature. DPM (70.0 g) and H$_2$O$_2$ (18.6 g; 0.19 mole; 30% aqueous) were added. The reaction was heated at 70° C. for 6 h. and deionized water was added (75.0 g). A clear solution of the desired product (about 30% solids) resulted.

Preparation of FC-4:

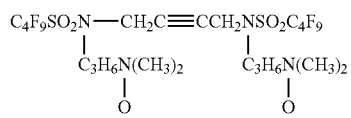

The procedure as described for the preparation of FC-3 was followed, substituting 1,4-dichloro-2-butyne (9.8 gram; 0.08 mole) for 1,2-dichloroethylene.

Preparation of FC-5:

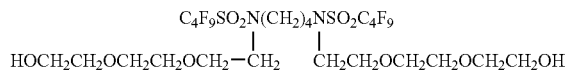

A 500 mL three-necked round bottom flask, fitted with a stirrer, heating mantle and condenser, was charged with C$_4$F$_9$SO$_2$NH(CH$_2$)$_4$NHSO$_2$C$_4$F$_9$ (65 g; 0.1 mol ), DMF (50 g) and heptane (30 g). A Dean Stark trap was added and all the heptane was removed. The mixture was cooled to about 40° C. under nitrogen, and NaOCH$_3$ (36.0 g; 0.2 mol; 30% solution in methanol) was added. The ensuing mixture was heated for 1 hour at 50° C. and the remaining methanol was distilled from the mixture. This mixture was cooled to about 40° C. under nitrogen, ClCH$_2$CH$_2$OCH$_2$CH$_2$OCH$_2$CH$_2$OH (33.6 g; 0.2 mol) was added an the mixture was heated overnight at 80° C. under nitrogen. The next day the mixture was filtered and deionized water (150 g) added. A clear solution of a the desired product resulted.

Preparation of FC-6:

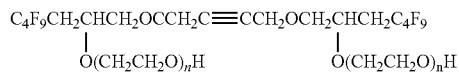

A 500 mL three-necked round bottom flask, fitted with a stirrer, heating mantle and Dean Stark trap, was charged with PBCH epoxide (27.6 g; 0.1 mol), heptane (50 g) and 1,4-dihydroxy-2-butyne (4.3 g; 0.05 mol). After setting up a Dean Stark trap, heptane (20.0 g) was distilled off to dry all chemicals and equipment. The mixture was cooled to about 40° C. under nitrogen and BF3 etherate (0.1 mL) was added and a Dewar cooler containing dry ice/acetone was added. Ethyleneoxide was bubbled through the mixture (22.0 g; 0.5 mol; at a rate of about 1 bubble per second). When addition was finished, the mixture was slowly warmed up to 60° C. under nitrogen and held for 1 hour. All remaining solvent was stripped off and a yellow-brown liquid, the desired compound, resulted.

All products were diluted to 1500 ppm in deionized water. Static surface tension was measured using a Kruss K-12 tensiometer and the Du Nouy ring method at 20° C. Dynamic surface tensions were measured at the same concentration using a Sensadyne 5000 Maximum Bubble Pressure Tensiometer (available from Data Physics Instruments, Germany) at a bubble speed of 4 bubbles/second at 20° C.

TABLE 1

| Example | Surfactant | Static Surf Tension (mN/m) | Dynamic Surf. Tension (mN:m) |
|---------|------------|---------------------------|------------------------------|
| 1 | FC-3 | 19.5 | 43.0 |
| 2 | FC-4 | 22.3 | 40.0 |
| 3 | FC-5 | 19.3 | 49.3 |
| 4 (at 500 ppm) | FC-6 | 25.2 | 55..0 |

Formulation of Floor Finish

An aqueous styrene-acrylic emulsion was used to evaluate surfactant performance. The floor finish was similar to the Shield-8 formulation (available from CCP, Kansas City Mo.), except that the standard fluorinated surfactant ("ZONYL FS") and the hydrosol emulsion leveler (("ESI-CRY 842") were removed to facilitate testing of new surfactants. Samples of this floor finish were prepared for testing by addition of 100 or 200 ppm of experimental surfactant (based on solids). Surfactants were generally pre-diluted to 1% solids in water or DPM (or a mixture thereof) prior to addition with stirring at room temperature to the liquid floor finish.

Five mL of the liquid floor finish, containing 100 or 200 ppm of fluorochemical surfactant was applied to the center of a 12"×12" pre-cleaned black vinyl composite floor tile, then spread using a with a piece of gauze or cheesecloth covering the entire surface area of the tile until an even coating is obtained. The coating was applied using figure eight strokes covering the entire surface area of the tile until an even coating is obtained. An "X" is then made in the coating from corner to corner of the tile. The process was repeated until a total of five layers of coating had been applied, allowing each coating layer to dry for at least 25-30 minutes prior to reapplication.

Gloss

The coated tiles were allowed to air dry for at least 7 days, then 60° gloss measured by a BYK-Gardner micro-TRI-gloss meter (available from Paul N. Gardner Co., Inc., Pompano Beach Fla.), taking the average of six different measurements over the surface of the tile. Higher gloss readings are considered desirable.

Wetting (0-5 Rating)

Wetting performance was determined by visually inspecting coating for surface defects during and after drying of final coat. Poor wetting is generally manifested as surface defects in the form of craters, pinholes, and the coating pulling in from the edges of the tile. Wetting performance values were determined as follows:

| Observation | Rating |
|-------------|--------|
| Complete de-wetting of the coating. Coating is mainly concentrated in small pools. | 0 |
| Extreme de-wetting. Only small areas of continuous coating. | 1 |
| Mainly continuous coating, however, coating has numerous craters and/or pinholes. Pronounced pulling from the edges. | 2 |

-continued

| Observation | Rating |
|---|---|
| Few but obvious craters and/or pinholes in coating | 3 |
| Very few pinholes are small craters; small lower gloss areas. | 4 |
| No observation of craters, pinholes, or coating pulling in from the edge. Wet coating remains smooth during dry down. Even gloss over entire surface. | 5 |

Leveling (0-5 Rating)

Leveling performance was also determined by visual inspection of the coating during and after drying of the final coat. Poor leveling can be determined through observation of figure eight strokes and the "X" applied during the coating process. The coating can appear uneven or have channels from application strokes. Leveling was evaluated using the following criteria:

| Observation | Rating |
|---|---|
| Deep channels or grooves in the X and figure eight pattern | 0 |
| Observation of X and all figure eight application strokes; uneven thickness of coating | 1 |
| Though the coating may appear smooth, can observe X and all 8's | 2 |
| Obvious observation of X and some figure eight patterns | 3 |
| Faint observation of X and little to no figure eight patterns | 4 |
| No observation of X or figure eights at any angle | 5 |

Foam (Y/N Rating)

Degree of foaming was determined visually during application of coating and was given a "Y" or "N" rating depending on whether there was significant foaming or not, respectively. Lower foaming ("N") is desirable in coating applications.

Performance ratings are listed in Table 1 (200 ppm by weight) and Table 2 (100 ppm by weight) below.

TABLE 2

| Example | Surfactant (200 ppm Loading) | Wetting (0-5 best) | Leveling (0-5 best) | 60° Gloss | Foam |
|---|---|---|---|---|---|
| 5 | FC-1 | 3.0 | 4.0 | 60 | N |
| 6 | FC-2 | 2.0 | 4.0 | 67 | N |
| C-1 | "FC-129" | 4.0 | 4.0 | 62 | Y |
| C-2 | "FC-120" | 4.0 | 5.0 | 64 | Y |
| C-3 | "ZONYL FSH" | 3.7 | 4.0 | 58 | Y |
| C-4 | "ZONYL FSN" | 4.0 | 4.0 | 58 | Y |
| C-5 | "MASURF FS-230" | 4.0 | 4.0 | 61 | Y |

TABLE 3

| Example | Surfactant (100 ppm Loading) | Wetting (0-5 best) | Leveling (0-5 best) | 60° Gloss | Foam |
|---|---|---|---|---|---|
| 7 | FC-1 | 4.0 | 4.0 | 56 | N |
| 8 | FC-2 | — | — | — | — |
| C-6 | "FC-129" | 4.0 | 4.0 | 62 | Y |
| C-7 | "FC-120" | 4.0 | 4.0 | 63 | Y |
| C-8 | ZONYL FSH" | 4.0 | 3.3 | 57 | Y |
| C-9 | "ZONYL FSN" | 3.0 | 3.0 | 61 | Y |
| C-10 | "MASURF FS-230" | 4.0 | 4.0 | 58 | Y |

Surfactant Performance in General Purpose, Waterborne, Acrylic, Wood Coating Resin A waterborne wood coating resin was prepared to evaluate surfactant performance. The resin was based on Neoresins Neocryl A-6092 all-acrylic base resin (provided by Neoresins, Wilmington Mass.). The base resin and other ingredients were formulated into Neoresins recommended WB-4041 starting point formulation The WB-4041 formulation normally comprises 100 parts by weight (pbw) Neocryl™ A-6092, 20 pbw water, 1 pbw ammonium hydroxide, 1.1 pbw KP-140™ (Great Lakes Chemicals), 13 pbw "CARBITOL" (available from Union Carbide, Danbury, Conn.), a 0.34 pbw COLLOID 770" (available from Rhodia, Cranbury, N.J.).

Once a stock solution of the starting point formulation was prepared, samples were taken and blended with 1000 or 2,500 ppm of experimental surfactant (based on solids) for testing. The surfactant of this invention was pre-diluted to 25 wt. % in "CARBITOL" prior to adding to the aqueous starting point formulation with stirring. Other commercial surfactants were used as received.

The following procedure was used for evaluation of leveling, wetting, foaming, surface tension, and gloss of the surfactant in a waterborne acrylic wood coating resin. Using a foam brush, an even coating of the formulation to be tested was applied to a 12×12 Maple plywood panel, and allowed to dry for at least 8 hours. A total of 3 coats were applied using this procedure. The first coat was lightly sanded with 150-200 grit sandpaper. During coating the degree of foaming (between 1-5; 5=best=least amount of foam) was observed.

After the third coat was dry, the coating was evaluated for craters and pinholes (dewetting problems) or brush marks and striations (leveling problems). Also measure 60° gloss according to the procedure described above.

The panels were rated between 1 and 5 for wetting and leveling and gloss values were recorded, using the test method described above. The surface tension of the remaining resin solution was measured using a tensiometer.

Final performance ratings are listed in Table 4 and Table 5.

TABLE 4

| Example | Surfactant (2500 ppm Loading) | Wetting (0-5 best) | Leveling (0-5 best) | 60° Gloss | Foam (0-5 best) | Surface Tension (dyne/cm) |
|---|---|---|---|---|---|---|
| 9 | FC-1 | 4.0 | 4.0 | 53 | 2.0 | 27.0 |
| 10 | FC-2 | — | — | — | — | — |
| C-11 | "FC-129" | 5.0 | 4.0 | 36 | 0.5 | — |
| C-12 | "FC-120" | 4.5 | 3.5 | 44 | 0.5 | — |
| C-13 | "ZONYL FSH" | 5.0 | 5.0 | 58 | 0.0 | — |
| C-14 | "ZONYL FSN" | 4.0 | 5.0 | 49 | 0.0 | — |
| C-15 | MASURF FS-230" | 4.0 | 4.0 | 32 | 0.0 | — |

TABLE 5

| Example | Surfactant (1000 ppm Loading) | Wetting (0-5 best) | Leveling (0-5 best) | 60° Gloss | Foam (0-5 best) | Surface Tension (dyne/cm) |
|---|---|---|---|---|---|---|
| 11 | FC-1 | 4.0 | 4.0 | 51 | 2.0 | 28.7 |
| 12 | FC-2 | — | — | — | — | — |
| C-16 | "FC-129" | 1.0 | 3.0 | 41 | 2.0 | 23.6 |
| C-17 | "FC-120" | 4.0 | 3.5 | 45 | 1.0 | 26.0 |
| C-18 | "ZONYL FSH" | 4.0 | 4.0 | 40 | 2.0 | 27.5 |
| C-19 | "ZONYL FSN" | 3.0 | 3.0 | 41 | 2.0 | 27.9 |
| C-20 | "MASURF FS-230" | 4.0 | 4.0 | 40 | 2.0 | 24.0 |

Surfactant Performance in Waterborne Polycarbonate-Urethane Dispersion for Use as Topcoat on Vinyl Flooring, Wood and Plastic A waterborne polycarbonate-urethane resin was prepared to evaluate surfactant performance. The base resin was Stahl's RU-40-415 formulation (obtained from Stahl, Peabody, Mass.) with the fluorinated surfactant removed. Samples of this stock resin dispersion were blended with 50 ppm of experimental surfactant (based on solids) for testing. The surfactants tested were pre-diluted to 1.0 wt. % by weight in water or a mixture of DPM and water prior to adding to the aqueous starting point formulation with stirring.

The same procedures used for evaluation of the waterborne acrylic wood coating resin described above were used for evaluation of the waterborne polycarbonate-urethane coating resin.

Final performance ratings are listed in Table 6 below.

TABLE 6

| Example | Surfactant (50 ppm Loading) | Wetting (0-5 best) | Leveling (0-5 best) | 60° Gloss | Foam (0-5 best) | Surface Tension (dyne/cm) |
|---|---|---|---|---|---|---|
| 13 | FC-1 | 4.0 | 5.0 | 67 | 4.0 | 36.1 |
| 14 | FC-2 | — | — | — | — | — |
| C-21 | "FC-129" | 3.5 | 4.5 | 58 | 2.0 | 36.7 |
| C-22 | "FC-120" | 3.0 | 4.0 | — | 3.0 | 39.2 |
| C-23 | "ZONYL FSH" | 4.0 | 4.0 | — | 3.0 | 42.1 |
| C-24 | "ZONYL FSN" | 3.0 | 3.0 | — | 3.0 | 42.0 |
| C-25 | "MASURF FS-230" | 3.0 | 4.0 | — | 3.0 | 36.6 |

What is claimed is:

1. A compound of the formula:

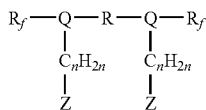

wherein
each $R_f$ is a fluoroalkyl group,
R is a divalent organic linking group,
Q is selected from —SO$_2$N(-)(-), —(CH$_2$)$_p$CH(O—)(-), and (CH$_2$)$_p$—CH(O—)(CH$_2$)$_p$O—, where p is an integer of 1 to 11,
Z is a hydrophilic group selected from amine oxide, sulfonate, sulfate, phosphate, and quaternary ammonium groups, and
each n is 0 to 11.

2. The compounds of claim 1 wherein $R_f$ is a C$_3$ to C$_{12}$ fluoroalkyl group.

3. The compounds of claim 1 wherein $R_f$ is a C$_3$ to C$_6$ perfluoroalkyl group.

4. The compounds of claim 1 of the formula:

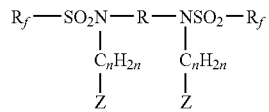

wherein
each $R_f$ is a fluoroalkyl group,
R is a divalent organic linking group,
Z is a hydrophilic group selected from amine oxide, sulfonate, sulfate, phosphate, and quaternary ammonium groups, and
each n is 0 to 11.

5. The compounds of claim 1 of the formula

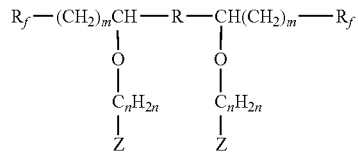

wherein
each $R_f$ is a fluoroalkyl group,
R is a divalent organic linking group,
Z is a hydrophilic group selected from amine oxide, sulfonate, sulfate, phosphate, and quaternary ammonium groups,
each m is 0 to 4, and
each n is 0 to 11.

6. The compounds of claim 1 of the formula

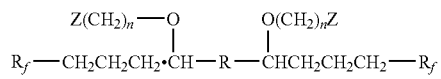

wherein
each $R_f$ is a fluoroalkyl group,
R is a divalent organic linking group,
Z is a hydrophilic group selected from amine oxide, sulfonate, sulfate, phosphate, and quaternary ammonium groups, and
each n is 0 to 11.

7. The compounds of claim 1 of the formula

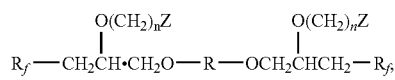

wherein
each $R_f$ is a fluoroalkyl group,
R is a divalent organic linking group,
Z is a hydrophilic group selected from amine oxide, sulfonate, sulfate, phosphate, and quaternary ammonium groups, and
each n is 0 to 11.

8. The compounds of claim 1 wherein R is a divalent aliphatic, cycloaliphatic, aromatic group, or combinations thereof.

9. The compounds of claim 1 wherein R is a divalent alkylene, alkenylene, or alkynylene.

10. The compounds of claim 1 where Z is $-SO_3^-M^+$, or $-N^+(R^1)_3Y^-$, where M+ is a metal or ammonium cation, $Y^-$ is an anion, s is 2-20, t is 0-20, and $R^1$ and $R^2$ are independently a hydrogen or a lower alkyl group.

11. A polymer composition comprising the compounds of claim 1 and a thermoplastic or thermoset polymer.

12. The polymer composition of claim 11 comprising 50 to 2500 ppm of the compounds of claim 1.

13. The composition of claim 11 wherein said thermoplastic polymers are selected from the group consisting of polyamides, polyesters, polyurethanes, acrylates and polyolefins.

14. A shaped article comprising the composition of claim 11.

15. The shaped article of claim 14 selected from the group of films, sheets and fibers.

16. The composition of claim 11 wherein said thermoset polymer is selected from polyurethanes, epoxy resins, epoxides and acrylates.

17. A surfactant composition comprising an aqueous solution of the composition of claim 1.

18. The surfactant composition of claim 17 comprising 0.001 to about 0.5 weight percent fluorochemical surfactant based on the weight of the solution.

19. A method of reducing the surface tension of a liquid comprising adding to said liquid a surfactant composition according to claim 17.

20. A method of improving the wetting of a coating mixture on a substrate comprising adding to the coating mixture a surfactant composition according to claim 17.

21. A coating composition comprising the fluorochemical surfactant of claim 1 and an organic resin.

22. The coating composition of claim 21 wherein said organic resin is a waterborne organic resin.

23. The coating composition of claim 21 wherein said organic resin is selected from epoxies, urethanes, polycarbonate-urethanes, alkyds and acrylics.

* * * * *

UNITED STATES PATENT AND TRADEMARK OFFICE
CERTIFICATE OF CORRECTION

PATENT NO. : 7,547,732 B2 Page 1 of 1
APPLICATION NO. : 11/215077
DATED : June 16, 2009
INVENTOR(S) : George G. I. Moore It is certified that error appears in the above-identified patent and that said Letters Patent is hereby corrected as shown below:

Column 4,
Line 63, delete "CCCH$_2$" and insert in place thereof -- CCH$_2$ --.

Column 12,
Line 33, delete "C$_2$H4N" and insert in place thereof -- C$_2$H$_4$N --.
Line 43, delete "C$_4$F$_9$SO$_2$NHC$_2$H$_4$SO$_2$C$_4$F$_9$" and insert place thereof
-- C$_4$F$_9$SO$_2$NHC$_2$H$_4$NHSO$_2$C$_4$F$_9$ --.

Column 13,
Line 42, delete "an" and insert in place thereof -- and --.

Column 17,
Line 62, Claim 1, delete "(CH$_2$)$_p$-CH(O-)(CH$_2$)$_p$O–" and insert in place thereof
-- –(CH$_2$)$_p$-CH(O-)(CH$_2$)$_p$O– --.

Signed and Sealed this

First Day of September, 2009

David J. Kappos
*Director of the United States Patent and Trademark Office*